(12) United States Patent
May et al.

(10) Patent No.: US 7,988,736 B2
(45) Date of Patent: Aug. 2, 2011

(54) METHOD AND APPARATUS FOR PROVIDING RESORBABLE FIXATION OF PRESS-FIT IMPLANTS

(75) Inventors: Brian M. May, Warsaw, IN (US); Philip Faris, Indianapolis, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 151 days.

(21) Appl. No.: 12/038,538

(22) Filed: Feb. 27, 2008

(65) Prior Publication Data

US 2009/0216325 A1 Aug. 27, 2009

(51) Int. Cl.
*A61F 2/38* (2006.01)
(52) U.S. Cl. .................... 623/20.17; 623/20.34
(58) Field of Classification Search ............... 623/11.11, 623/13.12, 13.18, 18.11, 20.14–20.17, 20.19, 623/20.21, 23.53, 23.55–23.59, 23.75, 20.34
See application file for complete search history.

(56) References Cited

U.S. PATENT DOCUMENTS

| | | | |
|---|---|---|---|
| 3,528,109 A | 9/1970 | Scalas | |
| 3,808,606 A | 5/1974 | Tronzo | |
| 4,355,429 A | 10/1982 | Mittelmeier et al. | |
| 4,840,632 A | 6/1989 | Kampner | |
| 4,990,161 A | 2/1991 | Kampner | |
| 5,021,062 A | 6/1991 | Adrey et al. | |
| 5,201,738 A | 4/1993 | Scott et al. | |
| 5,226,917 A | 7/1993 | Schryver | |
| 5,480,444 A * | 1/1996 | Incavo et al. ............... | 623/20.32 |
| 5,549,691 A | 8/1996 | Harwin | |
| 5,571,193 A | 11/1996 | Kampner | |
| 5,733,338 A | 3/1998 | Kampner | |
| 6,013,104 A * | 1/2000 | Kampner .................... | 623/22.17 |
| 6,296,667 B1 | 10/2001 | Johnson et al. | |
| 6,527,810 B2 | 3/2003 | Johnson et al. | |
| 6,605,090 B1 * | 8/2003 | Trieu et al. .................... | 606/281 |
| 2004/0260398 A1 | 12/2004 | Kelman | |
| 2005/0125068 A1 * | 6/2005 | Hozack et al. ............. | 623/20.32 |
| 2006/0093729 A1 | 5/2006 | Marx et al. | |

(Continued)

FOREIGN PATENT DOCUMENTS

DE 102004034331 2/2006

(Continued)

OTHER PUBLICATIONS

International Search Report and Written Opinion for PCT/US2009/035526 mailed Jun. 4, 2009 claiming benefit of U.S. Appl. No. 12/038,538 (the current case) filed Feb. 27, 2008.

(Continued)

*Primary Examiner* — Bruce E Snow
(74) *Attorney, Agent, or Firm* — Harness, Dickey

(57) ABSTRACT

A press-fit prosthesis for replacing a portion of a bone. The prosthesis can comprise a first side and a second side opposite the first side. The second side can be operable to engage the bone. The prosthesis can include at least one resorbable fixation member coupled to the second side such that the at least one resorbable fixation member does not extend through to the first side. The at least one resorbable fixation member can be coupled offset from a center of the second side. The at least one resorbable fixation member can substantially resist movement of the prosthesis relative to the bone. The at least one resorbable fixation member can resorb at a rate that enables bone in-growth to fixedly couple the prothesis to the bone.

16 Claims, 2 Drawing Sheets

U.S. PATENT DOCUMENTS

| | | | |
|---|---|---|---|
| 2006/0178749 A1* | 8/2006 | Pendleton et al. | 623/20.15 |
| 2006/0241776 A1 | 10/2006 | Brown et al. | |
| 2006/0241781 A1 | 10/2006 | Brown et al. | |
| 2007/0129809 A1 | 6/2007 | Meridew et al. | |
| 2007/0173948 A1 | 7/2007 | Meridew et al. | |
| 2007/0196230 A1 | 8/2007 | Hamman et al. | |
| 2007/0250175 A1 | 10/2007 | Meridew et al. | |
| 2008/0015691 A1* | 1/2008 | Wyss | 623/16.11 |
| 2008/0147187 A1 | 6/2008 | Bollinger et al. | |
| 2009/0084491 A1 | 4/2009 | Uthgenannt et al. | |

FOREIGN PATENT DOCUMENTS

| | | |
|---|---|---|
| EP | 0176711 | 4/1986 |
| EP | 1867301 | 12/2007 |

OTHER PUBLICATIONS

International Preliminary Report on Patentability and Written Opinion for PCT/US2009/035526 mailed Sep. 10, 2010 claiming benefit of U.S. Appl. No. 12/038,538 (the current case) filed Feb. 27, 2008.

* cited by examiner

METHOD AND APPARATUS FOR PROVIDING RESORBABLE FIXATION OF PRESS-FIT IMPLANTS

FIELD

The present disclosure relates generally to implants, and more specifically, to a method and apparatus for providing resorbable fixation of press-fit implants.

BACKGROUND

The statements in this section merely provide background information related to the present disclosure and may not constitute prior art.

Many portions of the human anatomy naturally articulate relative to one another. Generally, the articulation between the portions of the anatomy is substantially smooth and without abrasion. This articulation is allowed by the presence of natural tissues, such as cartilage and strong bone.

Over time, however, due to injury, stress, degenerative health issues and various other issues, articulation of the various portions of the anatomy can become rough or impractical. For example, injury can cause the cartilage or the boney structure to become weak, damaged, or non-existent. Therefore, the articulation of the anatomical portions is no longer possible for the individual.

At such times, it can be desirable to replace the anatomical portions with a prosthetic portion such that normal or easy articulation can be reproduced. For example, a distal end of a femur naturally articulates with respect to a tibia to form a knee joint. After injury or other degenerative processes, the distal end of the femur and the tibia can become rough or damaged. In these cases, it may be desirable to replace at least a portion of the tibia and/or femur with a prosthesis.

For example, a tibial tray can replace a portion of the tibia, and a polymer bearing can be positioned on the tibial tray to enable a femoral component to articulate relative to the bearing. Generally, tibial trays can include one or more bores that extend through the tibial tray for receipt of a mechanical fastener to couple the tibial tray to the tibia. The use of bores through the tibial tray, however, may allow wear debris to pass through the tibial tray.

SUMMARY

A press-fit prosthesis for replacing a portion of a bone. The prosthesis can comprise a first side and a second side opposite the first side. The second side can be operable to engage the bone. The prosthesis can include at least one resorbable fixation member coupled to the second side such that the at least one resorbable fixation member does not extend through to the first side. The at least one resorbable fixation member can be coupled offset from a center of the second side. The at least one resorbable fixation member can substantially resist movement of the prosthesis relative to the bone. The at least one resorbable fixation member can resorb at a rate that enables bone in-growth to fixedly couple the prothesis to the bone.

Further provided is a press-fit prosthesis for replacing a portion of a bone. The prosthesis can include a tray. The tray can be operable to replace the portion of the bone. The tray can include a first side that forms a barrier and a second side. The second side can be opposite the first side and can facilitate bone in-growth. The prosthesis can also include at least one resorbable fixation member coupled to the second side. The at least one resorbable fixation member can be adapted to be press-fit into a prepared portion of the bone to couple the tray to the bone. The at least one resorbable fixation member can include at least one formed geometric feature that can be operable to substantially resist movement of the tray relative to the bone. The at least one resorbable fixation member can resorb at a rate that enables bone in-growth to fixedly couple the second side of the tray to the bone.

Also provided is a press-fit prosthesis for replacing a portion of a bone. The prosthesis can include a tibial tray operable to replace a portion of a tibia. The tibial tray can have a bearing engaging surface that forms a barrier and a bone engaging surface. The prosthesis can include a bearing positioned on the bearing engaging surface of the tibial tray. The prosthesis can include a femoral component operable to replace a portion of a femur and articulate relative to the bearing. The prosthesis can also include a plurality of resorbable fixation members. The plurality of resorbable fixation members can be coupled to the bone engaging surface offset from a center of the bone engaging surface such that none of the plurality of resorbable fixation members are coupled to the center of the bone engaging surface and none of the plurality of resorbable fixation members extend through to the bearing engaging surface. The plurality of resorbable fixation members can be operable to be press-fit into the tibia to couple the tibial tray to the tibia. The plurality of resorbable fixation members can include at least one formed geometric feature that is operable to substantially resist movement of the tibial tray relative to the tibia. The plurality of resorbable fixation members can be composed of a bio-resorbable material selected from the group comprising: a resorbable polymer, a resorbable coral structure or combinations thereof. The bone engaging surface can comprise a porous metal or metal alloy structure. The plurality of resorbable fixation members can be operable to resorb at a rate that enables bone in-growth to fixedly couple the tibial tray to the tibia.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
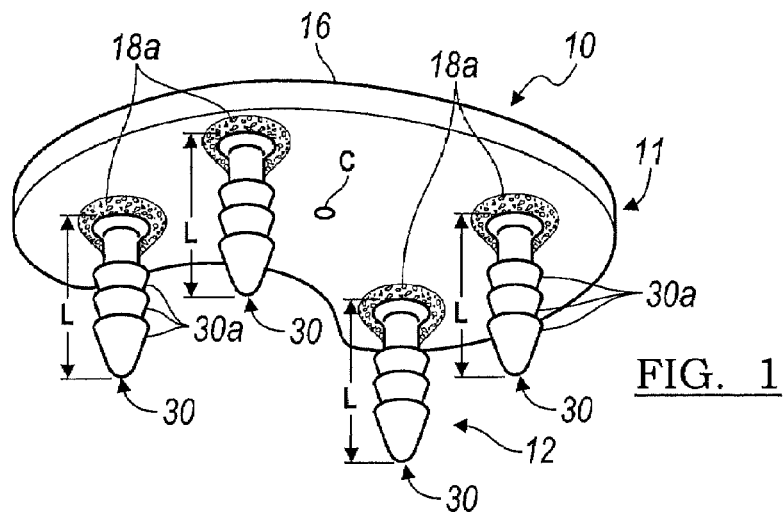
FIG. 1 is a perspective view of a system for resorbable fixation of a press-fit implant according to the present disclosure.

The following description is merely exemplary in nature and is not intended to limit the present disclosure, application, or uses. It should be understood that throughout the drawings, corresponding reference numerals indicate like or corresponding parts and features. Although the following description is related generally to a prosthesis that can be positioned in a prepared portion of the anatomy, such as in a tibia, it will be understood that the prosthesis, as described and claimed herein, can be used with any appropriate surgical procedure. Therefore, it will be understood that the following discussions are not intended to limit the scope of the appended claims.

Figure 3:
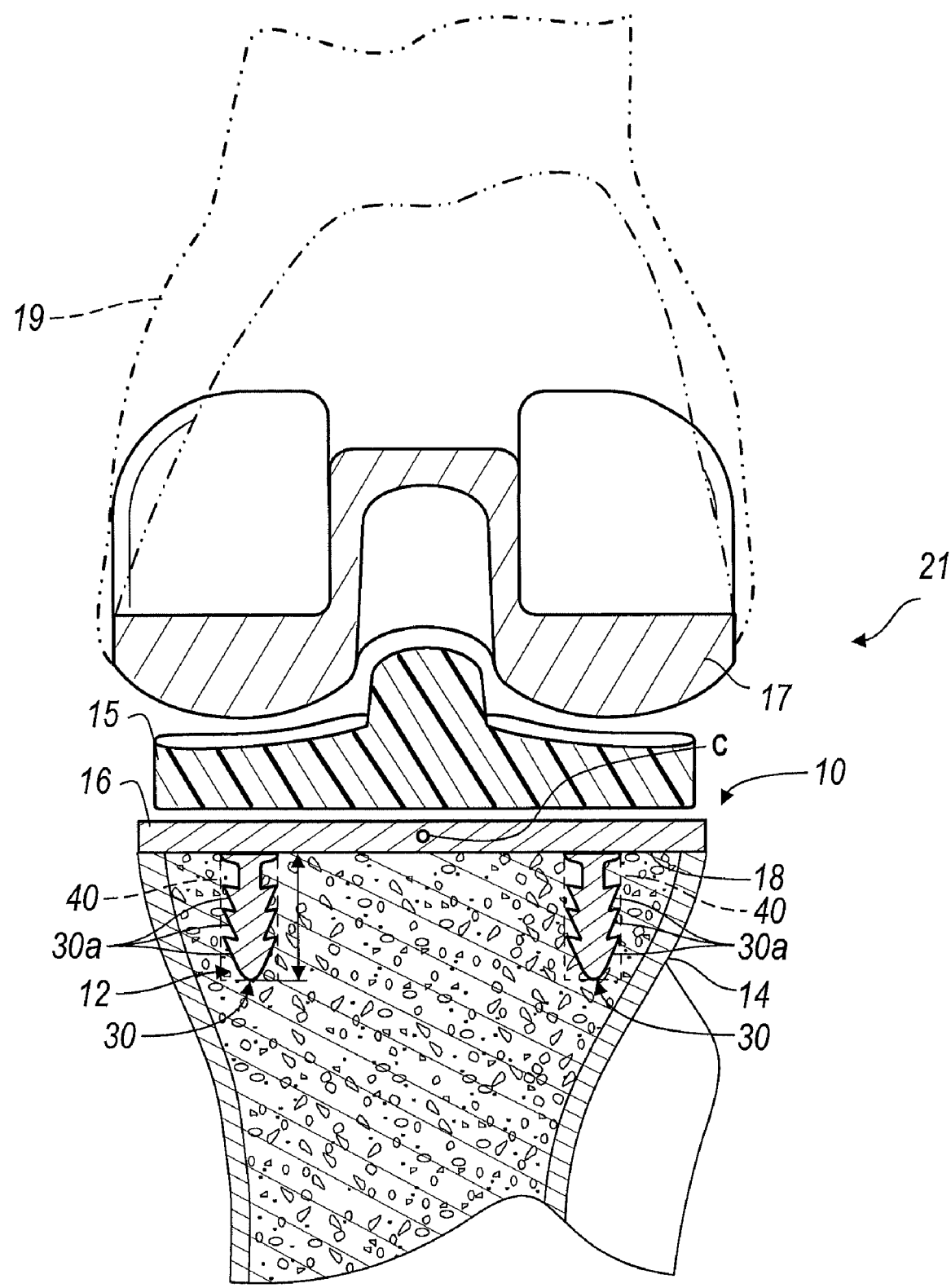
FIG. 3 is a schematic environmental view of the system of FIG. 1 in an anatomy.

With reference to FIG. 1, a press-fit tibial implant 10 is shown. The tibial implant 10 can include a tibial tray 11 and a resorbable fixation system 12 that can couple the tibial implant 10 to a tibia 14 (FIG. 3). A polymeric bearing 15 can be positioned atop the tibial tray 11. The bearing 15 can articulate with a femoral component 17 attached to a femur 19. The tibial tray 11 can include a bearing engaging surface 16 that engages the bearing 15, and a bone engaging surface 18 that engages the tibia 14. The bearing engaging surface 16 can engage the bearing 15 such that the bearing 15 can be fixedly coupled, floating or rotatable relative to the bearing engaging surface 16 of the tibial tray 11. The tibial tray 11 and bearing 15 can facilitate or enable the smooth articulation of the femoral component 17 with respect to the tibia 14 to form a knee joint 21.

It should be noted that the tibial tray 11 can be used with any suitable knee prosthesis, such as a Vanguard™ complete knee system, a cruciate retaining knee prosthesis, for example, the AGC® Total Knee System™, a posterior stabilized knee prosthesis, for example, the AGC® Tradition High-Post Knee System™, or a hinged knee prosthesis, for example, the Orthopaedic Salvage System™, all provided by Biomet, Inc. of Warsaw, Ind., and the remainder of the knee prosthesis can be configured as needed for the particular surgical application. It will be understood, however, that although the resorbable fixation system 12 is described herein as being used with the tibial tray 11, the resorbable fixation system 12 could be employed with any suitable implant, such as an acetabular cup of a hip prosthesis, a glenoid head of a shoulder prosthesis, a femoral component of a knee prosthesis, a femoral component of a hip prosthesis, an elbow prosthesis, a wrist prosthesis, a unicondular prosthesis, etc.

With continued reference to FIG. 1, the tibial tray 11 can comprise any suitable biocompatible material, such as a biocompatible metal, metal alloy or polymer. For example, suitable materials can comprise cast titanium, titanium alloy, stainless steel, ceramic bone substitutes, etc. The bearing engaging surface 16 can be substantially devoid of apertures or bores through the tibial tray 11, which can prevent wear debris from passing through the tibial tray 11 and into the surrounding bone of the tibia 14. Thus, the tibial tray 11 can serve as a barrier between the bearing 15 and the tibia 14.

As shown in FIG. 3, the bone engaging surface 18 can be disposed adjacent to a prepared portion of the tibia 14, and can be opposite the bearing engaging surface 16. In one example, as shown in FIGS. 1 and 3, the bone engaging surface 18 can comprise a substantially planar surface, which can be formed integrally with the bearing engaging surface 16. In some instances, the bone engaging surface 18 can include a roughened portion 18a to facilitate bone in-growth. The roughened portion 18a can comprise at least one of a porous coating, a porous layer, a collagen foam, a ceramic layer or the like that can enable bone in-growth to form and thereby couple the tibial tray 11 to the tibia 14.

Figure 2A:
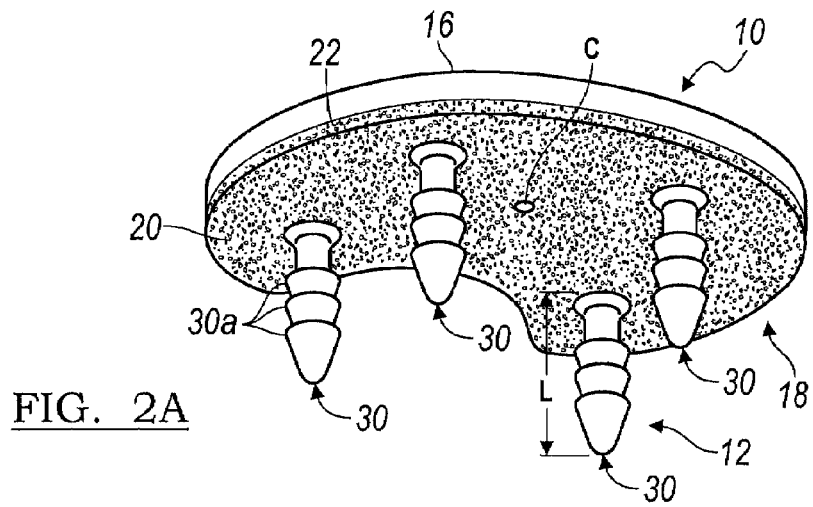
FIG. 2A is a perspective view of a system for resorbable fixation of a press-fit implant according to the present disclosure.

In another example, as shown in FIG. 2A, the bone engaging surface 18 can comprise a biocompatible porous metal or metal alloy three-dimensional structure 20 that can be coupled to an intermediate surface 22. The porous structure 20 can be coupled to the intermediate surface 22 via any suitable technique, such as sintering, welding, etc. The porous structure 20 can enable additional bone in-growth to form, which can further couple the tibial tray 11 to the tibia 14. In addition, it should be noted that the porous structure 20 can be coated with an antibiotic, bone growth enhancing material, or the like, to promote healing and bone integration. The porous structure 20 can comprise Regenerex™, provided by Biomet, Inc. of Warsaw, Ind., for example, however, any suitable biocompatible porous metal or metal alloy structure could be employed. As a further example, additional exemplary porous metal materials and exemplary methods for making porous metal can be found in co-pending applications, U.S. Ser. No. (11/357,929, filed Feb. 17, 2006), entitled "Method and Apparatus for Forming Porous Metal Implants," U.S. Ser. No. (11/709,549, filed Feb. 22, 2007), entitled "Porous Metal Cup with Cobalt Bearing Surface," and U.S. Ser. No. (11/111,123 filed, Apr. 21, 2005; Ser. No. 11/294,692, filed Dec. 5, 2005; Ser. No. 11/357,868, filed Feb. 17, 2006, and Ser. No. 11/546,500 filed Oct. 11, 2006), each entitled "Method and Apparatus for use of Porous Implants," all assigned to Biomet Manufacturing Corp. of Warsaw Ind., and incorporated herein by reference. The resorbable fixation system 12 can be directly coupled to the porous structure 20, or could be coupled to the intermediate surface 22 such that the resorbable fixation system 12 extends through and beyond the porous structure 20, as will be discussed.

Figure 2B:
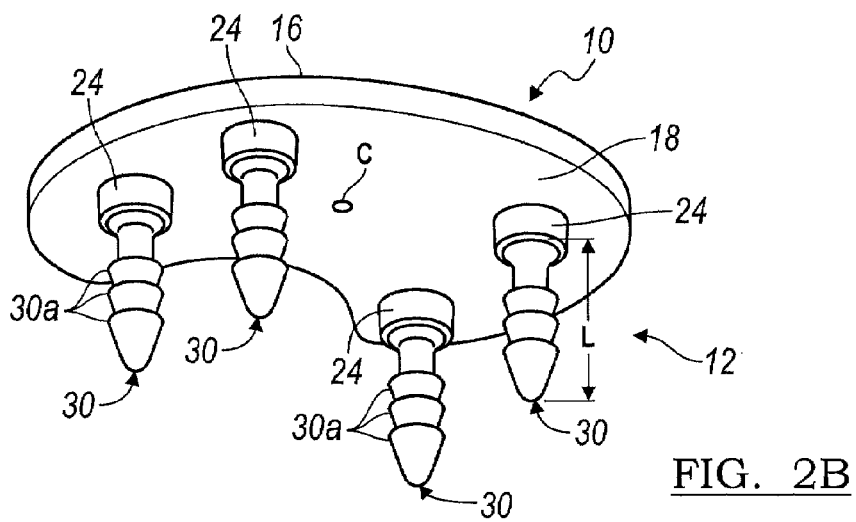
FIG. 2B is a perspective view of a system for resorbable fixation of a press-fit implant according to the present disclosure.

In addition, according to various embodiments, with reference to FIG. 2B, the bone engaging surface 18 can include one or more coupling features 24 to assist in coupling the resorbable fixation system 12 to the bone engaging surface 18, if desired. For example, the coupling features 24 can comprise annular protrusions that can extend from the bone engaging surface 18. It should be noted, however, that any type of coupling features 24 could be employed, if desired, such as threaded apertures, conical protrusions, apertures, notched protrusions, rectangular or polygonal protrusions, grooves, etc. The coupling features 24 can assist in coupling the resorbable fixation system 12 to the tibial tray 11, however, it should be noted that the coupling features 24 can be optional, and the resorbable fixation system 12 can be directly coupled to the bone engaging surface 18 or tibial tray 11.

The resorbable fixation system 12 can include one or more resorbable fixation members 30. Generally, the resorbable fixation members 30 can be arranged about a center C of the tibial tray 11, and typically can be arranged offset from the center C of the tibial tray 11. For example, two resorbable fixation members 30 can be coupled at a medial position on the tibial tray 11, and two of the resorbable fixation members 30 can be coupled at a lateral position on the tibial tray 11. The use of a plurality of resorbable fixation members 30 about the center C of the tibial tray 11 eliminates the need for a central post to couple the tibial tray 11 to the anatomy, which can reduce stress-shielding of the tibia 14. The resorbable fixation members 30 can be directly coupled to the bone engaging surface 18, or can be coupled to the coupling features 24 of the bone engaging surface 18. In this regard, if the bone engaging surface 18 does not include the coupling features 24, then the resorbable fixation members 30 can be formed directly on the bone engaging surface 18.

If, however, the bone engaging surface 18 includes the coupling features 24, then the resorbable fixation members 30 can be configured to be coupled to the bone engaging surface 18, via the coupling features 24. For example, if the coupling features 24 comprise threaded apertures, then the resorbable fixation members 30 can include threads to enable the resorbable fixation members 30 to be threadably coupled to the tibial tray 11. If, for example, the coupling features 24 comprise protrusions, such as cylindrical protrusions, then the resorbable fixation members 30 can be molded or formed onto the protrusions, as shown in FIG. 2B. If the bone engaging surface 18 includes the porous structure 20 as shown in FIG. 2A, then the resorbable fixation members 30 can be coupled directly to the porous structure 20 by molding, for example. Further, the resorbable fixation members 30 can be coupled to the intermediate surface 22 such that the resorbable fixation members 30 extend through and beyond the porous structure 20, via a mechanical fastening technique, such as the use of mechanical fasteners, a press-fit, a snap-fit, etc. Generally, however, the resorbable fixation members 30 can be coupled to the bone engaging surface 18 such that none of the resorbable fixation members extend through to the bearing engaging surface 16.

The resorbable fixation members 30 can be composed of any suitable resorbable material, such as a resorbable polymer, a resorbable coral structure or combinations thereof. In addition, the resorbable material can also comprise Lactosorb® available from Biomet Inc. of Warsaw, Ind., which comprises 82% L-Lactic acid and 18% glycolic acid.

The resorbable fixation members 30 can have a length L that can be selected based on the type of resorbable material to control the resorption rate of the resorbable fixation members 30. In this regard, the resorbable fixation members 30 can be configured such that the resorption of the resorbable fixation members 30 can occur at a rate substantially equal to the rate it takes for bone in-growth or bone integration to occur. Thus, at a certain point in time, the resorbable fixation members 30 can be resorbed by physiological processes, which can cause the loss of strength of the resorbable fixation members 30, but by that time, the bone integration can rigidly couple the tibial tray 11 to the anatomy. The use of the resorbable fixation members 30 can reduce the potential for stress shielding of the tibia 14 as the resorbable material does not provide long-term fixation. Rather, long-term fixation is provided by the bone in-growth on the tibial tray 11. Further, the use of the resorbable fixation members 30 can reduce the need for mechanical fasteners, such as screws, to couple the tibial tray 11 to the anatomy. By eliminating the need for mechanical fasteners, the need for bores extending through the tibial tray 11 can also be eliminated, which can thereby prevent wear debris from passing through the tibial tray 11.

The resorbable fixation members 30 can have a shape that enables the resorbable fixation members 30 to be press-fit into a prepared portion of the anatomy, while also preventing movement of the tibial tray 11 relative to the anatomy. For example, the resorbable fixation members 30 can comprise one or more formed geometric features 30a, such as barbs, discs, etc. that can be sized to resist movement of the tibial tray 11 relative to the tibia 14 (FIG. 3). As a further example, the resorbable fixation members 30 can comprise a polygonal shape, such as triangular, octagonal, octoangular or could comprise cylindrical projections, spherical projections, tapered projections, cruciate projections or any combination of the above.

In order to couple the tibial tray 11 to the anatomy, the tibial tray 11 can be prepared. In this regard, if the bone engaging surface 18 comprises the porous structure 20, then the porous structure 20 can be coupled to the intermediate surface 22 opposite the bearing engaging surface 16 (FIG. 2A). Then, the resorbable fixation members 30 can be coupled to the bone engaging surface 18. If the bone engaging surface 18 comprises the coupling features 24, as illustrated in FIG. 2B, then the resorbable fixation members 30 can be coupled to the coupling features 24. If the bone engaging surface 18 does not include the coupling features 24, as shown in FIG. 1, then the resorbable fixation members 30 can be molded or formed directly onto the bone engaging surface 18. In either event, the resorbable fixation members 30 can generally be formed offset from the center C of the tibial tray 11. With the resorbable fixation members 30 coupled to the bone engaging surface 18, the tibial tray 11 can be prepared for insertion into the anatomy.

With reference to FIG. 3, prior to coupling the tibial tray 11 to the anatomy, the anatomy, such as the tibia 14, can be prepared as is generally known in the art. The anatomy can generally be prepared to include reamed apertures 40 (shown in phantom) that can correspond with the number of resorbable fixation members 30 coupled to the tibial tray 11. Then, the tibial tray 11 can be press-fit into the anatomy, and the resorbable fixation members 30 can engage the apertures 40 in the anatomy. It will be understood, however, that the apertures 40 are optional, and the resorbable fixation members 30 could be press-fit into the tibia 14 without the use of reamed apertures 40. Generally, the tibial tray 11 can be pressed into the anatomy until the bone engaging surface 18 is adjacent to the anatomy. The resorbable fixation members 30, when fully retained within the apertures 40, can resist the movement of the tibial tray 11 relative to the anatomy in all planes, and can further provide stability to the tibial tray 11 until bone integration occurs. Over time, bone in-growth can occur, such that the bone integration can couple the tibial tray 11 to the anatomy, and at that time, the resorbable fixation members 30 can be substantially resorbed through physiological processes.

While specific examples have been described in the specification and illustrated in the drawings, it will be understood by those of ordinary skill in the art that various changes can be made and equivalents can be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. A press-fit prosthesis for replacing a portion of a bone comprising:
   a tibial tray devoid of apertures passing there through having:
     a medial portion;
     a lateral portion;
     a center portion between the medial portion and the lateral portion;
     a first side; and
     a second side opposite the first side, the second side operable to engage the bone; and
   a pair of first resorbable fixation members coupled to the second side at the medial portion and a pair of second resorbable fixation members coupled to the second side at the lateral portion, the resorbable fixation members do not extend through to the first side, the resorbable fixation members are coupled offset from the center portion of the second side, the resorbable fixation members substantially resist movement of the prosthesis relative to the bone;

wherein the resorbable fixation members resorb at a rate that enables bone in-growth to fixedly couple the prosthesis to the bone;

wherein the center portion is devoid of a fixation member; and wherein the second side includes a roughened portion confined to an area immediately surrounding each of the resorbable fixation members, each of the roughened portions are separate and spaced apart from one another.

2. The prosthesis of claim 1, wherein the first side defines a bearing engaging surface that forms a barrier that continuously extends from the first side to the second side and the second side comprises a bone engaging surface.

3. The prosthesis of claim 2, wherein the bone engaging surface is selected from the group consisting of a porous metal structure, a porous metal alloy structure, a solid metal structure, a solid metal alloy structure, a porous coating, and combinations thereof.

4. The prosthesis of claim 2, wherein the first side is without holes and the resorbable fixation members extend from only the second side.

5. The prosthesis of claim 2, wherein the resorbable fixation members are each molded onto the bone engaging surface.

6. The prosthesis of claim 2, further comprising:
a bearing positioned on the bearing engaging surface of the tibial tray and extending entirely across the medial portion, the center portion, and the lateral portion; and
a femoral component that articulates relative to the bearing to form a knee joint, the femoral component including a medial condyle, a lateral condyle, and a center portion that extends from the medial condyle to the lateral condyle to connect the medial condyle to the lateral condyle.

7. The prosthesis of claim 2, wherein none of the resorbable fixation members are coupled to the center portion of the bone engaging surface.

8. The prosthesis of claim 3, wherein the porous metal or metal alloy structure, the solid metal or metal alloy structure, and the porous coating cover less than an entirety of the bone engaging surface.

9. The prosthesis of claim 1, wherein the resorbable fixation members each include at least one feature to enable the tibial tray to be press-fit into two bores formed in the medial side of the bone and two bores formed in the lateral side of the bone.

10. The prosthesis of claim 9, wherein the at least one feature is selected from the group consisting of a barb, a cylinder, a cruciate form, a projection, a polygon, a cone, a disk, a sphere, and combinations thereof.

11. The prosthesis of claim 9, wherein the bone is a tibia; and
wherein the prosthesis is press-fit into the tibia along a longitudinal axis of the tibia.

12. The prosthesis of claim 9, wherein the at least one feature is sized to engage the plurality of bores formed in the bone such that the prosthesis does not substantially move relative to the bone.

13. The prosthesis of claim 1, wherein the resorbable fixation members are each composed of a bio-resorbable material selected from the group consisting of a resorbable polymer, a resorbable coral structure, and combinations thereof.

14. The prosthesis of claim 1, wherein the second side includes a plurality of coupling features in only the medial and lateral portions that are each operable to couple one of the resorbable fixation members to the tibial tray.

15. The prosthesis of claim 14, wherein each of the coupling features include one of an annular protrusion extending from the second side, a threaded receptacle, a conical protrusion, an aperture, a notched protrusion, a rectangular protrusion, or a polygonal protrusion.

16. The prosthesis of claim 1, wherein the roughened portion includes at least one of a porous coating, a porous layer, a collagen foam, or a ceramic layer.

* * * * *